(12) United States Patent
Shim et al.

(10) Patent No.: US 11,555,806 B2
(45) Date of Patent: Jan. 17, 2023

(54) PORTABLE FLUID SENSORY DEVICE WITH LEARNING CAPABILITIES

(71) Applicant: ALPHA M.O.S, Toulouse (FR)

(72) Inventors: Chang-Hyun Shim, Fourquevaux (FR);
Philippe Benezech, Balma (FR);
Sandrine Isz, Toulouse (FR);
Jean-Christophe Mifsud, Goudourville (FR)

(73) Assignee: ALPHA M.O.S., Toulouse (FR)

( * ) Notice: Subject to any disclaimer, the term of this patent is extended or adjusted under 35 U.S.C. 154(b) by 190 days.

(21) Appl. No.: 15/552,640

(22) PCT Filed: Feb. 23, 2016

(86) PCT No.: PCT/EP2016/053783
§ 371 (c)(1),
(2) Date: Aug. 22, 2017

(87) PCT Pub. No.: WO2016/135146
PCT Pub. Date: Sep. 1, 2016

(65) Prior Publication Data
US 2018/0340921 A1    Nov. 29, 2018

(30) Foreign Application Priority Data

Feb. 27, 2015   (EP) .................................... 15305304

(51) Int. Cl.
*G01N 30/62*    (2006.01)
*G01N 33/49*    (2006.01)
*G16Z 99/00*    (2019.01)

(52) U.S. Cl.
CPC ......... *G01N 30/62* (2013.01); *G01N 33/4925* (2013.01); *G16Z 99/00* (2019.02); *Y02A 50/20* (2018.01)

(58) Field of Classification Search
CPC .... G01N 30/62; G01N 33/4925; G06F 19/00; Y02A 50/20
(Continued)

(56) References Cited

U.S. PATENT DOCUMENTS 5,980,830 A * 11/1999 Savage .............. G01N 33/4925
422/555
2003/0164312 A1* 9/2003 Prohaska ............... G01N 30/64
205/783.5

(Continued)

FOREIGN PATENT DOCUMENTS

CN    101073007 A    11/2007
CN    101261280 A    9/2008

(Continued)

OTHER PUBLICATIONS http://www.mcb.unibremen.de/shared/Flyer.pdf downloaded Aug. 23, 2017.

(Continued)

*Primary Examiner* — Benjamin R Whatley
*Assistant Examiner* — Jacqueline Brazin
(74) *Attorney, Agent, or Firm* — Meagher Emanuel Laks Goldberg & Liao, LLP

(57) ABSTRACT

The invention discloses a device for identifying fluids or measuring their concentration. The device is configured to capture fluid sensing signals and sent to processing capabilities to be annotated, pre-processed and fed to databases of datasets and models which have learning capabilities. The device has a stick or stylus form factor which is makes it fit to be used by health care professionals or by the general public. Advantageously, the stick can be used to capture data from gas and liquid, being possibly phases of the same analyte. The device can be a package containing all processing capabilities being configured to be autonomous. It (Continued)

can operate in conjunction with an intermediary device of a smart phone, a PC or a POCT type. The system comprising autonomous fluid sensory devices, intermediary devices and database servers can operate in a learning mode or in a use mode. Measurements can be filtered, and normalized to statistically eliminate the differences in measurements due to bad operational conditions, differences of device configurations or differences of local parameters (temperature, hygrometry, flow rate, etc. . . . ).

9 Claims, 9 Drawing Sheets

(58) Field of Classification Search
USPC .......................................................... 422/89
See application file for complete search history.

(56) References Cited

U.S. PATENT DOCUMENTS

| | | | |
|---|---|---|---|
| 2004/0004545 A1 | 1/2004 | Early | |
| 2004/0259265 A1* | 12/2004 | Bonne | G01N 30/08 436/151 |
| 2006/0155486 A1 | 7/2006 | Walsh et al. | |
| 2006/0163143 A1* | 7/2006 | Chirica | B01D 61/18 210/321.84 |
| 2006/0289809 A1* | 12/2006 | Bonne | G01N 27/622 250/504 R |
| 2010/0139363 A1* | 6/2010 | Klee | G01N 30/40 73/23.27 |
| 2011/0126124 A1* | 5/2011 | Bernard | G06Q 10/10 715/751 |
| 2011/0172931 A1* | 7/2011 | Murthy | G16C 20/20 702/32 |
| 2013/0244336 A1* | 9/2013 | Mayer | G01N 33/0004 436/147 |
| 2014/0083173 A1* | 3/2014 | Rapp | B01L 3/502715 73/61.59 |
| 2014/0223995 A1 | 8/2014 | Buhler et al. | |
| 2015/0343144 A1* | 12/2015 | Altschul | A61M 31/002 604/503 |
| 2018/0284758 A1* | 10/2018 | Celia | G05B 13/028 |
| 2020/0111342 A1* | 4/2020 | Hummer | G06K 19/0717 |

FOREIGN PATENT DOCUMENTS

| | | |
|---|---|---|
| CN | 101308152 A | 11/2008 |
| CN | 103308650 A | 9/2013 |
| CN | 103499665 A | 1/2014 |
| CN | 103728348 A | 4/2014 |
| CN | 103913484 A | 7/2014 |
| EP | 2 639 582 A1 | 9/2013 |
| EP | 2 533 037 A1 | 12/2017 |
| JP | 2002350422 A | 12/2002 |
| WO | WO-2005095924 A1 * 10/2005 ......... G01N 15/0826 |  |
| WO | 20090037289 A1 | 3/2009 |
| WO | 2010/071428 A1 | 6/2010 |
| WO | 2012/033999 A2 | 3/2012 |
| WO | 2012168444 A1 | 12/2012 |
| WO | 2013/099238 A | 7/2013 |

OTHER PUBLICATIONS http://www.mems.ece.vt.edu/research.php?id=19 downloaded Oct. 3, 2017.
http://www.toshiba.co.jp/about/press/2014_03/pr1801.htm Mar. 18, 2014.
http://math.stanford.edu/~muellner 2009.
Paliwal, 'Neural networks and statistical techniques: A review of applications' in Expert Systems with Applications vol. 36, Issue 1, Jan. 2009, pp. 2-17.
Chorowski et al. "Review and performance comparison of SVM- and ELM-based classifiers" in Expert Systems with Applications vol. 36, Issue 1, Jan. 2009, pp. 2-17.
Stephen Grossberg "Adaptive Resonance Theory: How a brain learns to consciously attend, learn, and recognize a changing world", Centre for Adaptive Systems, Boston University, Neural Networks, Elsevier Ltd, 37 (1-47) 2013.
Jung-Hwan Cho*, Chang-Hyun Shim**, In-Soo Lee+, Duk-Dong Lee*, and Gi-Joon Jeon, "An Embedded system for real time gas monitoring using an ART2 neural network", School of Electrical Engineering and Computer Science, Kyungpook National University, Daegu, Korea, ICCAS; Oct. 22-25, 2003.
International Search Report for PCT/EP2016/053783, dated Mar. 24, 2016.
International Written Opinion for PCT/EP2016/053783, dated Mar. 24, 2016.
Costas Neocleous, Christos Schizas, "Artificial Neural Network Learning: A Comparative Review" in Methods and Applications of Artificial Intelligence Lecture Notes in Computer Science, vol. 2308, 2002, pp. 300-313.
English translation of Japanese Office Action issued for JP 2017-545298, dated Mar. 10, 2020.
English translation of 2nd Chinese Office Action issued for CN 201680012379.5, dated Mar. 2, 2020.
English translation of 1st Chinese Office Action issued for CN 201680012379.5, dated Apr. 2, 2019.

* cited by examiner

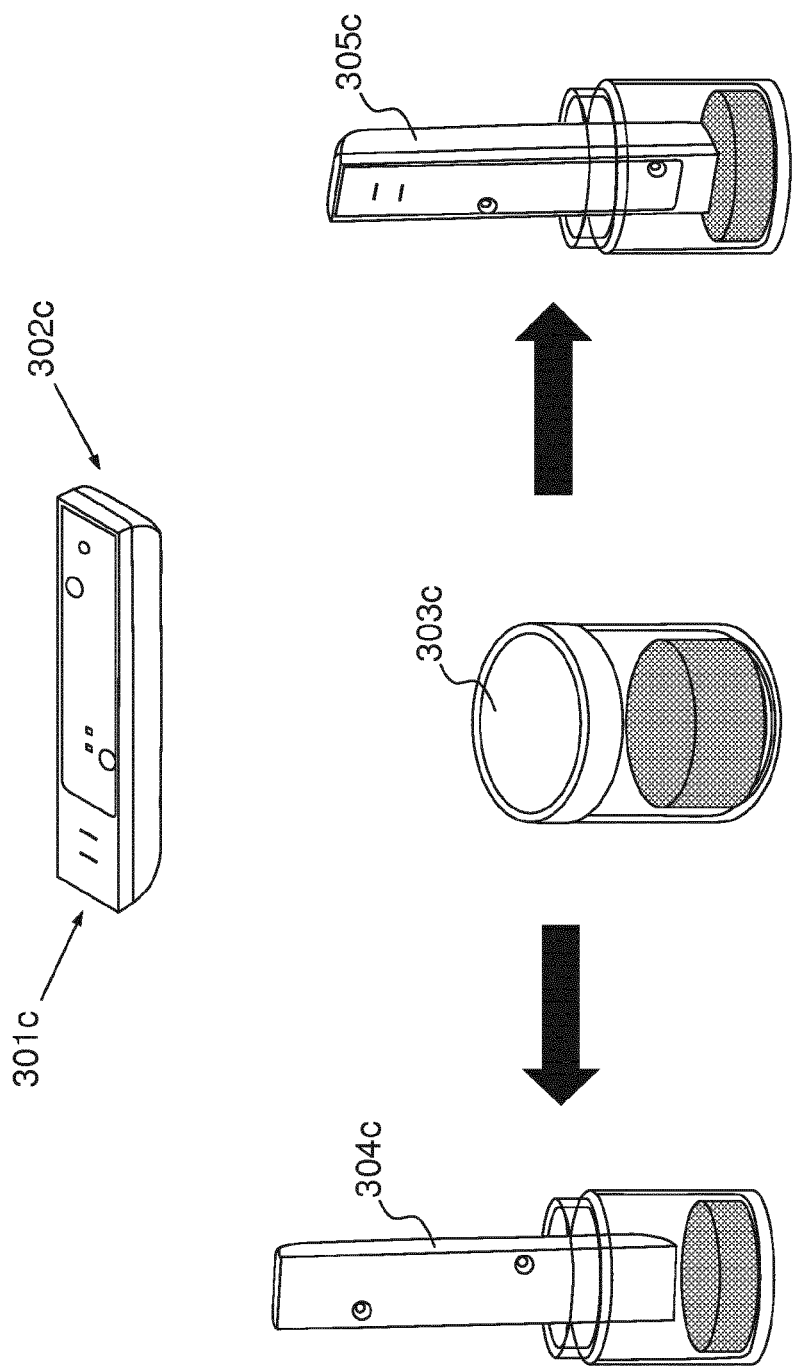

PORTABLE FLUID SENSORY DEVICE WITH LEARNING CAPABILITIES

FIELD OF THE INVENTION

The present invention notably applies to the field of e-sensing, i.e. systems and/or devices comprising physical sensors, signal and data processing capabilities used to detect and/or identify (or measure the concentration of) analytes in a gas or liquid carrying phase. More specifically, it applies to miniature devices with communication capabilities.

BACKGROUND

Environmental concerns create a need for the general public in an urban environment to easily access information about the concentration of a gas or particles in the atmosphere at their place. Likewise, water pollutants may need to be detected, either at the tap or in rivers, or on the sea shore. Also, hazards in the chain of production, transportation or preservation of food elements have created a need for the detection of bacteria proliferation, which may be detected by their odor. And health monitoring applications can benefit from breath data. These are only a few examples of the functions that the public at large could use in a miniature fluid sensory device.

To respond to such needs, it is known in the art to assemble sensors in sensor cells which may be sensitive to different compounds to be analyzed. Such cells can then be packaged together with an electronic device with processing and communication capabilities, like a smart phone. This is for instance the case of the device disclosed in European patent application published under n°2639582.

But a first drawback of a device of this type is that it cannot be used to detect and analyze compounds in a liquid phase because the communication device cannot be immersed in water. Therefore, its field of application is limited to gaseous phases. Also, this device only uses the communication capabilities of the smart phone with which it is integrated. Finally, but it is not the least problem to be solved, this prior art device has only the capabilities to send measurements to a server and receive the results of an identification performed on a server.

There is therefore a need for a more versatile device which would be capable to analyze a broader variety of analytes in liquid as well as in gaseous phases, and to do this possibly in communication with a number of different devices. There is also a need for a device which could be part of a network of data processing capabilities for an improved accuracy of identification of the compounds to be analyzed.

SUMMARY OF THE INVENTION

It is an object of the invention to provide these improvements over the prior art.

It achieves this target by providing a fluid sensory device with learning capabilities.

To this effect, the invention discloses a fluid sensory device comprising, in a package: a fluid sensor for sensing an analyte and generating a fluid sensing signal; a communication capability configured to send to a first processing capability a first dataset representative of the fluid sensing signal, wherein said first dataset further comprises a label characterizing the fluid sensing signal, said label being created at one of the communication capability and the first processing capability.

Advantageously, the fluid sensor comprises a gas sensor.

Advantageously, the gas sensor includes a single semiconducting metal-oxide element.

Advantageously, the gas sensor comprises one of an array and a stack of a plurality of semiconducting metal-oxide elements.

Advantageously, the fluid sensory device of the invention further comprises a source of ultraviolet light for illuminating at least some of the plurality of semiconducting metal-oxide elements.

Advantageously, the gas sensor comprises a micro gas chromatograph.

Advantageously, the fluid sensory device of the invention has an entry port with a bell shaped extension.

Advantageously, the fluid sensor comprises a liquid sensor.

Advantageously, the liquid sensor comprises a micro HPLC column.

Advantageously, the fluid sensory device of the invention, having an elongated form factor with an end comprising a contact surface of the liquid sensor.

Advantageously, an entry port is covered with a removable cap which is usable as a cup for receiving a sample to be analyzed and the fluid sensory device.

Advantageously, the fluid sensory device of the invention further comprises an additional sensor selected in a group comprising temperature sensors, flow sensors and hygrometry sensors, an output of the additional sensor being transmitted to the processing capability.

The invention also discloses a method to produce a model for identifying at least one of a nature of a first fluid and a concentration of said first fluid in a second fluid, said method comprising: receiving, at a first processing capability, a first dataset representative of at least one of a nature of the first fluid and a concentration of said first fluid in the second fluid, said first dataset comprising a label characterizing a fluid sensing signal; combining, at the first processing capability, said first dataset with a second dataset comprising at least one of a text, a sound and an image, representative of at least one of a nature of the first fluid and a concentration of said first fluid in the second fluid; transmitting from the first processing capability to a second processing capability the first dataset and the second dataset; classifying, at the second processing capability, a plurality of pairs of first datasets and second datasets from a plurality of first processing capabilities, said classifying based on a classifying of the plurality of second datasets; selecting for each class at the output of the classifying a statistical model correlating the plurality of first datasets and the plurality of second datasets, said statistical model fit for the nature of the first fluid; calculating parameters of the statistical model for each class from the plurality of pairs of first datasets and second datasets.

Advantageously, one of the first dataset and the second dataset further comprises at least a value of one of a temperature, a pressure and a hygrometry measurement at a location of the fluid sensory device.

Advantageously, the second dataset further comprises data to localize the first processing capability.

The invention also discloses a method for identifying at least one of a nature of a first fluid and a concentration of said first fluid in a second fluid, said method comprising: receiving, from a fluid sensory device, at a first processing capability, said first processing capability located in the vicinity of the fluid sensory device, a first dataset representative of at least one of a nature of the first fluid and a concentration of said first fluid in the second fluid; retrieving, from a second processing capability, at the first processing capability, a plurality of statistical models produced by the method of producing a model according to the invention; selecting a statistical model from the plurality of statistical models; inputting the first dataset in the statistical model at the output of the selection; if the at least one of a nature of a first fluid and a concentration of said first fluid in a second fluid is identified, outputting the result at the first processing capability; if the at least one of a nature of a first fluid and a concentration of said first fluid in a second fluid is not identified, redoing at least one of the selecting and the retrieving of a statistical model until either the result is obtained or a stop criteria is met.

The invention also discloses a processing capability, a computer program configured to execute at least one of the methods of the invention, as well as a system comprising a plurality of fluid sensory devices, a plurality of intermediary devices and a database server.

The invention brings to health care and environment professionals, as well as to the general public, the benefit of advanced electronic sensing technologies thus far confined to the world of instrumentation. The use of advanced signal, data processing technologies, statistical analysis and modeling methods enables the creation of vast amounts of data which enables improved accuracy of identification of analytes of interest for the well being of the public.

BRIEF DESCRIPTION OF THE DRAWINGS

The invention will be better understood and its various features and advantages will become apparent from the description of various embodiments and of the following appended figures:

FIGS. 3a, 3b and 3c represent use cases of the fluid sensory device, to illustrate possible physical configurations of the device of the invention and its accessories, in a number of its embodiments;

DETAILED DESCRIPTION

Figure 1A:
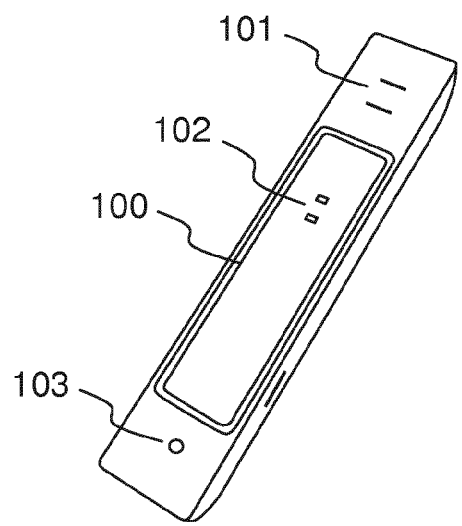
FIGS. 1a, 1b and 1c represent a fluid sensory device in a number of embodiments of the invention, from different viewing angles.
Figure 1B:
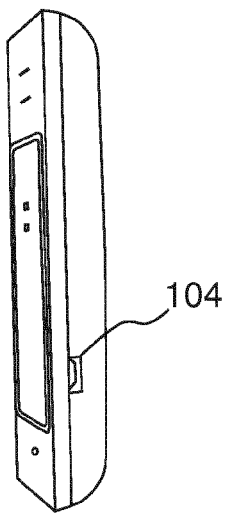
Figure 1C:
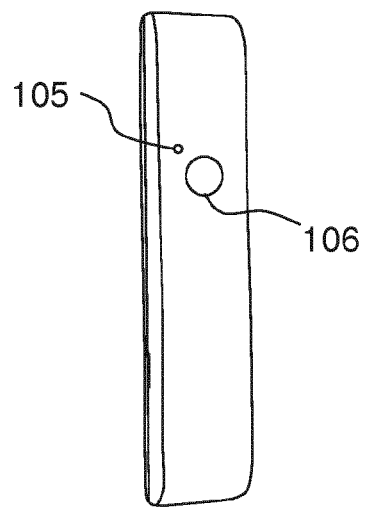

FIGS. 1a, 1b and 1c represent a fluid sensory device in a number of embodiments of the invention, from different viewing angles.

In the context of the invention, we construe a fluid as being a carrying phase, said phase being either gaseous or liquid and possibly carrying a single or multiple compounds to be analyzed (the analytes). The analytes may be dispersed in the carrying phase in a solid state, a liquid state or a gaseous state. The analytes may be an odor, a savor or another property which may be perceptible to human or animal senses or a substance which, without being perceptible to human or animal senses can impact his/her/its well being.

A fluid sensory device 100 according to the invention primarily comprises entry ports 101 for the fluid and fluid sensors (not shown) in a package. According to certain aspects of the invention, the package of the device is of a 3D form factor resembling a parallelepiped or a cylinder, with a length which is much longer than the dimensions of a 2D section. The package has two ends which may have a section which is smaller than a section of the package at the middle. The package of the fluid sensory device may be held by a user as a stick or as a stylus. The stick form factor may allow the user to have the device hold more easily in a vertical position, possibly in a specific box used to hold samples to be analyzed. The stylus form factor, where the device has an end proximal to the user, when the user holds the device, and a distal end. The distal end can be configured so as to be used to enter data in another device, like a smart phone equipped which a touch screen.

The form factors of the devices displayed in FIGS. 1a, 1b and 1c are therefore only exemplary embodiments of a device according to the invention, shaped in a parallelepiped stick form factor. These examples are in no way limiting of the scope of the invention. In these examples, the dimensions have been adapted so that the stick is easy to carry. Alternatively, the form factor of the stick can be cylindrical, or partially cylindrical and partially conical. Advantageously, the larger dimension (width or diameter of the largest section) will be smaller than 50 mm. When the form factor is a parallelepiped, the thickness will be smaller than 25 mm. More advantageously, the larger dimension (width or diameter of the largest section) will be smaller than 25 mm and, when the form factor is a parallelepiped, the thickness will be smaller than 20 mm. The length of the stick may be between 100 and 250 mm.

For different applications, other form factors may be more adequate. A flat form factor may for instance be adequate to detect a liquid on its lower side and a gas on its upper side.

An entry port for a gas sample to be analyzed can be located at one of the ends of the device or on one of its sides. Also, there may be an exit port, distinct from the entry port for the gas, to be let out of the device. Or the entry port can also operate as an exit port. The entry port can be configured with capillary tubes and/or with chicane barriers, so as to control the flow of gas reaching the sensor. In the case where the sample to be analyzed is blown by a human or animal user, the velocity of the gas entering the port will vary significantly depending on the user. The arrangement with capillary tubes and/or chicane barriers will level the differences and normalize the measurements. A man of ordinary skill will know how to design and dimension such an arrangement. When capillary tubes are included, those will typically have a diameter between 0.1 and 2 mm and a length of between a few mm and a few cm.

Alternatively or in addition, a miniature pump, a manual pump (rubber sucker) or a micro-ventilator can be used to control the flow either in the entry port or in the exit port. An example of a commercial reference of a miniature pump which can be used to perform the intended function is KPM10A from Koge Electronics™. An example of a commercial reference of a micro-ventilator is HY_10A03A from Sepa™. The pump can be used either continuously or being commanded to function either for a given period of time or when the pressure/flow rate falls below a determined threshold. The pressure and/or flow rate are being controlled with a combination of the pump, a pressure/flow rate sensor and a control loop.

Similar configurations can be applied for entry ports for a liquid fluid. A same device may have two entry ports, one for a liquid fluid, and the other for a gas fluid, possibly the gas phase of the same liquid. The flow of liquid fluids may be advantageously regulated using filters in addition or as a substitute to chicanes/capillary tubes. Exemplary embodiments of the invention of such a configuration are commented upon below in relation with FIG. 3c.

Needless to say that the device should have no dead volume and the sensor chamber volumes should be as small as possible.

Devices according to the invention are especially suitable for use with miniature sensors, such as Micro Electro Mechanical Systems or MEMS. Miniature sensors are already available for these applications. For analyzing gas samples, Metal Oxide on Silicon or MOS sensors can be used. MOS sensors have a resistivity which varies with the concentration of a specific gas in the sample. Surface Acoustic Wave sensors or SAW sensors and Quartz Micro-Balanced sensors or QMB sensors are capable of measuring the mass of a compound in a gas. Conducting polymers, electrochemical, capacitive, optical sensors, including infra-red or near infrared active or passive sensors, photon ionization detectors (PID) can also be used. Output can be change of color, fluorescence, conductivity, vibration, etc. . . . . Examples of MOS sensors which can be used in the device of the invention are sensors which can be purchased from E2V Technologies™, with reference MICS-5914, which are specific to ammonia ($NH_3$), from SGX Sensortech, with reference MICS-5524, which can measure the concentration of carbon monoxide (CO), ethanol ($C_2H_6OH$), hydrogen ($H_2$), ammonia ($NH_3$) and methane ($CH_4$), or from Figaro Engineering™, with reference TGS-8100, which has high sensitivity to a number or indoor air contaminants, such as cigarette smoke or cooking odors.

Sensors of these types can be arranged in arrays, each sensor in the array being sensitive to a different compound. Arrangements of this type are disclosed by EP2639582 which was already cited.

Also, the applicant of the present application has co-invented arrangements of sensors in stack of the type disclosed by PCT application published under n°WO2012/168444 co-assigned to the applicant of the instant application. These sensors can be based on metal oxide or polymer materials or a combination thereof. They are arranged in stacks where layers in the stack will be made of materials chosen for their different reactivity to possible components of a gas to be analyzed. It is possible to assemble arrays of sensors of these types in a single portable package, so that a variety of gases/odors can be detected, identified and their concentration measured.

It is also possible to use as gas sensors assemblies of one or more micro gas chromatography columns, wherein the interior of each column is covered with a reactant to a specific gas, the specific gas being identified at the exit of the micro column by a peak of concentration corresponding to a specific retention time. Micro gas chromatography columns having dimensions which are compatible with the maximum dimensions cited above for the device of the invention are being developed, notably by the Microsystems Center of the Bremen University http://www.mcb.uni-bremen.de/shared/Flyer.pdf or by VirginiaTech VT MEMS lab http://www.mems.ece.vt.edu/research.php?id=19

Liquid sensors can be of different types such as optical, magnetic, electrochemical sensors including chemical field effect transistors (ChemFET), interdigitated electrodes, capacitive and impedance technique. Micro High Performance Liquid Chromatography (HPLC) columns can also be used, like those marketed by Exsigent™ (Micro LC200 Plus).

Fluid sensors have the common characterizing feature that temperature in the vicinity of the sensor has to be controlled. Thus, the sensors in the stick can be warmed up by micro heaters or light produced by infrared rays. They can also be cooled down with a thermo-plate using the Seebeck or Peltier effect. The thermo-active components can be either arranged on the sensor ship or at the entry port of the flow. The regulation will be done through a thermo sensor 103 like a Pt resistor or a thermo-couple. To control humidity, the stick can be provided with humidity filters or membranes well-known to the skilled persons like silica gel or polytetrafluoroethylene (PTFE) membranes. It is to be noted that a physical barrier can be put to analyze a gas dissolved in a liquid. Temperature/humidity sensors are provided by Sensirion™, like SHT-10, or Texas Instruments, like TMP-007. A flow sensor can also be inserted in the entry and/or the exit ports, if any. Flow measurement is used either to control the power of a pump to regulate the fluid flow or to normalize the fluid sensor output. Such sensors are provided by Omron™ (D6F-V03A1). It may be advantageous to provide the combination of fluid, flow, temperature and humidity sensors in the sensor platform.

The response of the sensors will therefore depend upon the composition of the analyte and physical parameters which will be monitored during measurement.

Humidity and temperature can be measured and regulated. Or a compensation can be applied to the fluid sensor responses at the time of processing the measurement data. It may be advantageous to control and regulate these parameters at ambient temperature at the location of the measurement and then compensate the measurements at various locations by the values of ambient temperature/humidity at given locations. The device should first be calibrated at the manufacturing plant and then at the site of measurement for more precision. Software calibration will also be available in the case where the device works with a system where a server contains large amount of data of various sources.

It will be advantageous to provide a memory in the device where a one or more configuration files will be stored containing information about the type of sensors, their characterizing parameters and their history of calibration. This information can be transmitted to a processing capability where the measurements will be analyzed. The memory will also be used to store software models to analyze the sensed data and identify the fluid, as will be explained further down in the description.

The device can be provided with an embedded processing capability (not shown in the figures), but it can also be operated by transmitting all its data to an outside processing capability. The device will be generally provided with a communication capability, for instance a micro USB port 104, which can also be used to recharge the batteries of the device (not shown in the figures). Alternatively or in addition, a Wifi, Bluetooth, Orthogonal Sequence Spread Spectrum (OSSS) or Ultra Narrow Band (UNB) communication capability (not shown in the figures) may also be provided.

The device will generally be provided with some LEDs, 102, to display its state (battery charged/in charge; analysis in progress/no analysis, for example); an On/off button 106, and possibly, a reset button 105.

As an option, a display or a simple additional LED (not shown in the figures) can be provided to allow an indication of the results of the measurements or to display an alarm. The fluid sensory device of the invention can be embodied in an object of everyday's life, for instance in a chopstick to measure the quality of food being consummated in a restaurant or at home. In other use cases or in addition to a visual alarm, the alarm can be sonic.

Figure 2A:
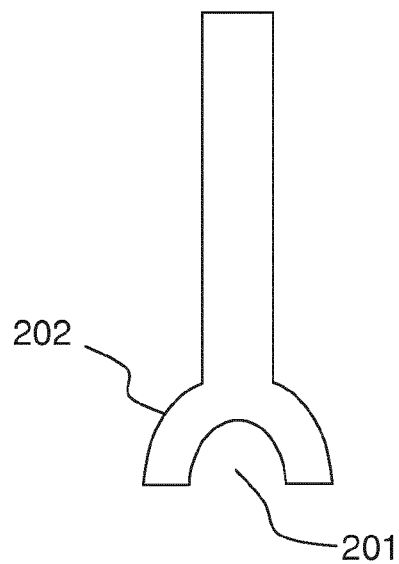
FIGS. 2a, 2b and 2c represent three variants of a fluid sensory device, adapted to control the operational conditions of capture of the fluid, in a number of embodiments of the invention.
Figure 2B:
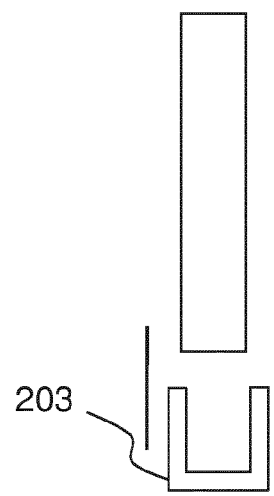
Figure 2C:
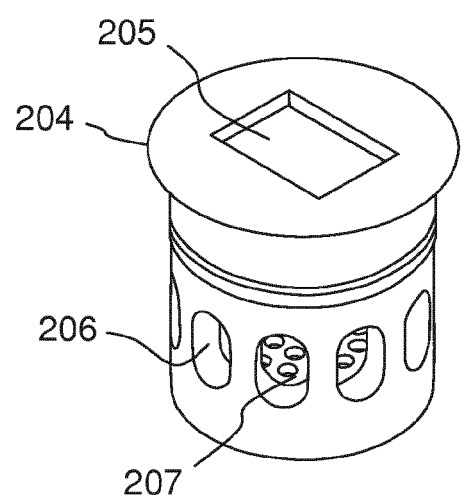

FIGS. 2a, 2b and 2c represent three variants of a fluid sensory device, adapted to control the operational conditions of capture of the fluid, in a number of embodiments of the invention.

This approach consists of bringing stability to a fluid sensory device by having measurement conditions in the stick as close as possible to the controlled conditions of the laboratory. This means equipping the stick with elements to set the measurement conditions (temperature, humidity, pressure, air flow . . . ) to values as close as possible to the conditions of reference measurements in the laboratory in order to reduce the variability of measurements.

As displayed in FIG. 2a, to control the headspace 201, a cavity can be used, with no flow, only diffusion, though small openings or/and filters so that the odor/gas can reach the sensor in the device. The device can have a small open cavity/bell, 202, in order to generate the sample headspace in a closed space with minor influence of the outer atmosphere. Natural diffusion of the sample will allow measurements by the sensor in the device.

In another embodiment displayed in FIG. 2b, a small cup 203 is configured to fit the bottom of the stick to close the headspace (like a pen/stylus cap). This cap is filled with samples and put on the stick to close the volume and then work in static mode (no gas flow). In this case, the samples can be placed up to a defined volume (possibly marked on the cup inside) or up to a given weight using a load cell (weight sensor) at the bottom of the cup together with a temperature sensor. Electric contacts are arranged with electrodes on both parts (cup and stick).

In FIG. 2c, is displayed an accessory 204, with a hole 205 configured to engage the device, when it is in a stick or stylus form factor. The lateral holes 206 will let the flow of sample in through the smaller holes 207 to allow a regular diffusion of the gas when entering the entry port. This configuration allows a better stability of the conditions of measurement (flow, temperature, humidity).

Figure 3A:
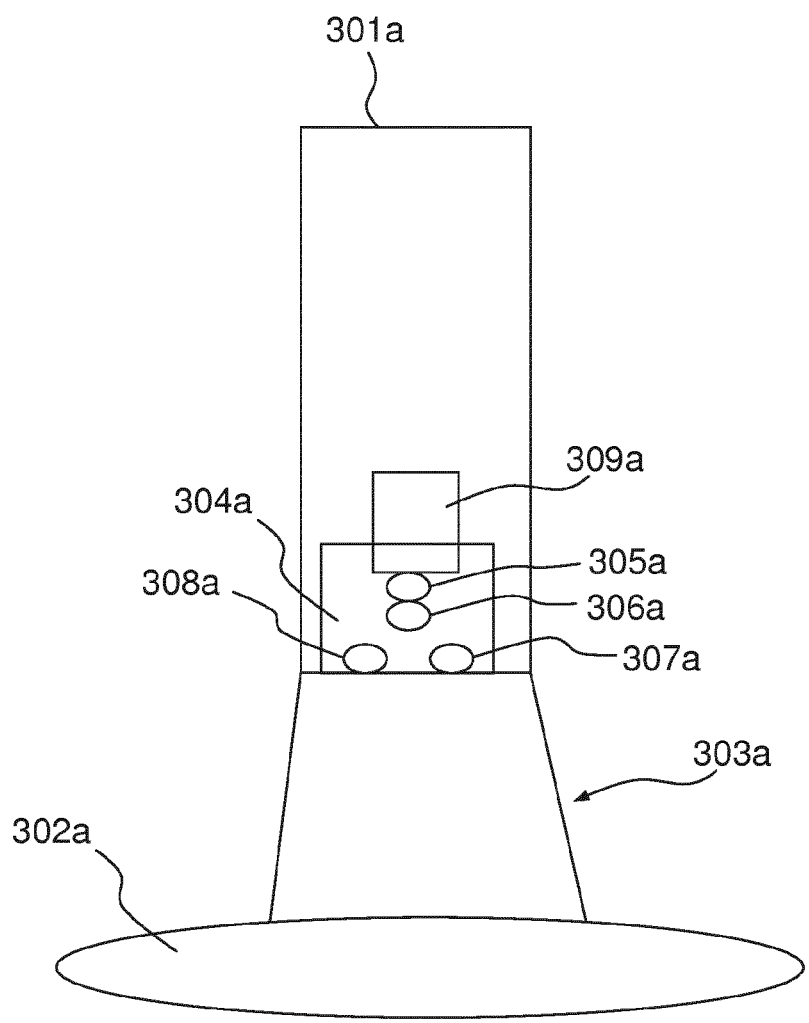
Figure 3B:
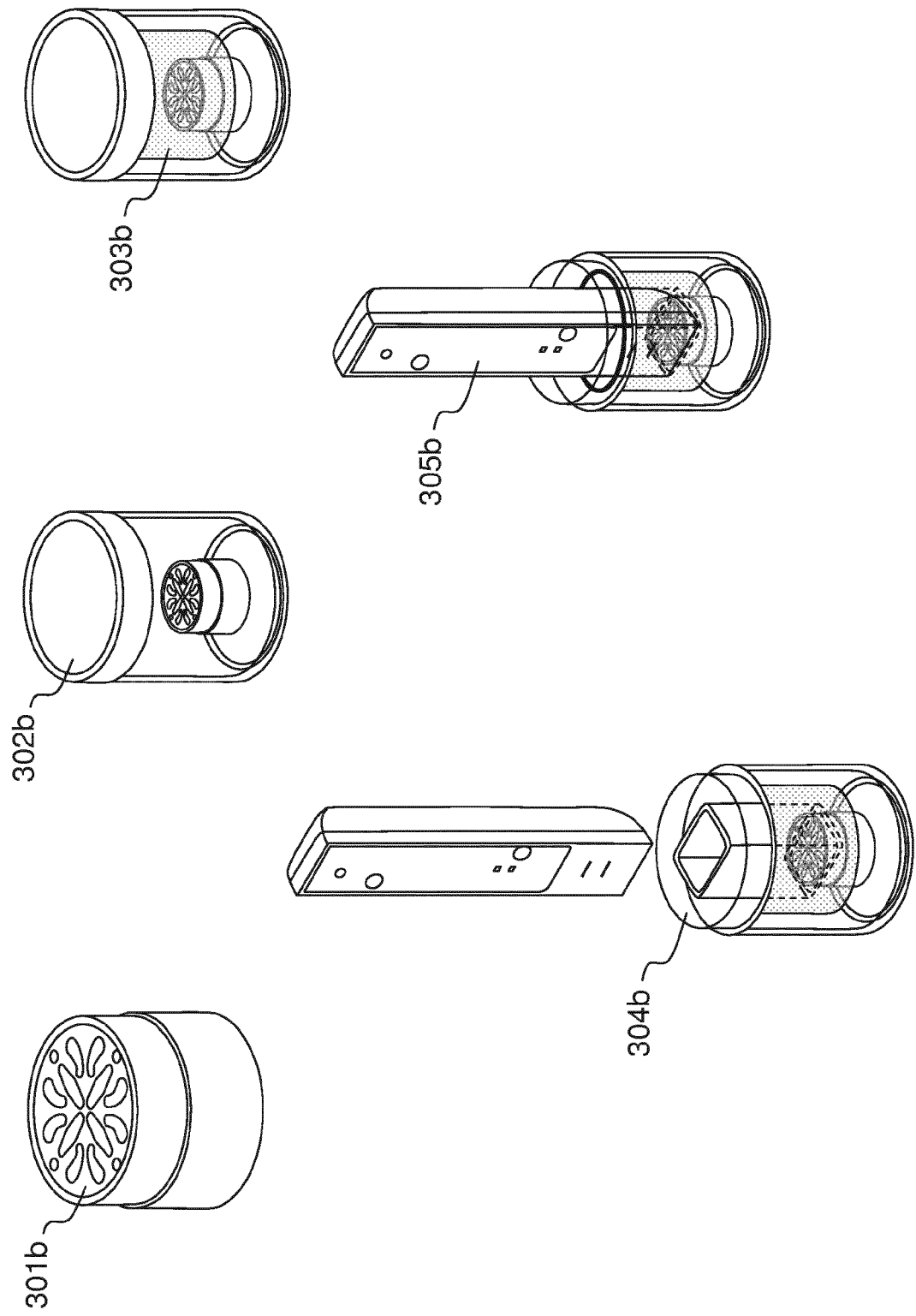

FIGS. 3a, 3b and 3c represent use cases of the fluid sensory device, to illustrate possible physical configurations of the device of the invention and its accessories, in a number of its embodiments.

In the use case depicted in FIG. 3a, an analyte 302a, possibly degassing a gas phase, such as a piece of food, like fish, is analyzed using a device according to the invention, 301a. The device is provided with extended lids, 303a (possibly substantially closing the space above the solid object). The device has an inner chamber, 304a, which comprises: a gas sensor, 305a, a flow sensor, 306a, a temperature and humidity sensor for measuring the ambient atmosphere, 307a, and an IR sensor 308a to measure a surface temperature of the fish. The device is also provided with a suction pump, 309a.

In FIG. 3b, is depicted a use case where small samples degassing gas/odor phases can fit in a container 301b. The container can be put in an analysis chamber with a lid, 302b. A specific arrangement 303b, 304b can be provided for a device 305b according to the invention, in a stick or a stylus form factor, to hold in a vertical position when engaged in said device.

FIG. 3c displays a device according to an embodiment of the invention with a liquid sensor 302c at one end of a stick and a gas sensor 301c, either at the other end or on a side of the stick at a distance of the end of the liquid sensor which would allow a gas phase above a liquid phase of the same analyte to be measured at the same time. The same analysis chamber 303c can be used to perform a gas sample analysis, 304c and a liquid sample analysis 305c, but two different analysis chambers can also be used. Typical examples of analytes where correlation of measurements of a gaseous phase and a liquid phase can improve identification are beverages, like sodas, wines, beers or juices.

Figure 4:
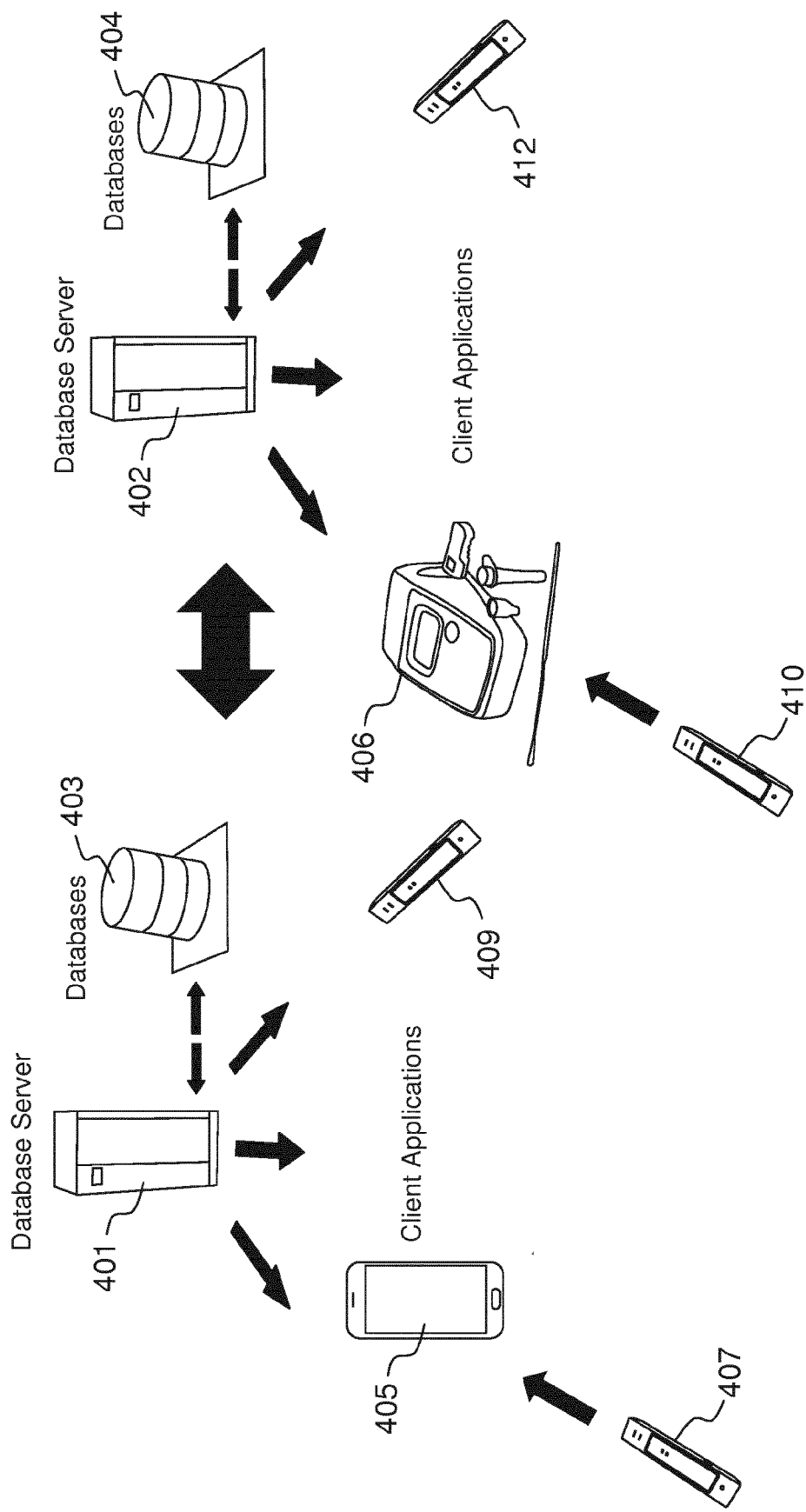
FIG. 4 represents a functional architecture of a fluid detection system with learning capabilities, in a number of embodiments of the invention.

FIG. 4 represents a functional architecture of a fluid detection system with learning capabilities, in a number of embodiments of the invention.

Database servers 401, 403 collect measurement data from processing capabilities 405, 406, or directly from fluid sensory devices. Corresponding temperature, pressure, flow rate, humidity data, as well as localization and/or other kind of annotations (text, sound, images) are also collected by the database servers at the same time as the measurement data, together called context or annotation data. The measurement data and annotation data are filtered and normalized. They are used to build various types of model or adjust their parameters, different types of models being adapted for different applications. Data processing and modeling techniques to obtain identification data (i.e. the identity/concentration of a fluid for a set of measurement data) will be described further down in the description. Measurement data, annotation data, models and identification data are stored in databases 402, 404. There is no need of a specific physical location for the databases and the database servers. They can be located in the "cloud", provided that security and safety rules, as well as privacy policies are implemented to protect sensitive data.

The database servers can communicate with the processing capabilities or the fluid sensory devices by any type of channel, be it a terrestrial metropolitan or local area network, a satellite network or a cellular network. Identification techniques known in the art will be used to secure access to the reserved database resources.

Processing capability 405 may be a smart phone, with localization (Global Navigation Satellite System, possibly augmented or substituted by other systems) and other annotation capabilities. For instance, a smart phone may be used to type or record identification data. It can also be used to capture an image of the analyte, as will be explained below. In certain embodiments, a number of devices of the invention may be connected to a standard personal computer (PC). This can be the case for instance when a trainer wants to monitor breathing of his team of cyclists, runners or other kinds of sportsmen. Another use case is where a consumer wants to test the quality of products stored in his fridge.

Processing capability 406 may be a specialized device, like a Point Of Care Testing equipment (POCT). POCT is available for a wide variety of tests like, blood gas analysis, cardiac monitoring, ultrasound imaging, diabetes examination, urine analysis. POCT equipment can be used by a practitioner with patients in a home care environment. It is advantageous to be able to use a fluid sensory device in combination with the POCT equipment, so that a number of measurements can be gathered in synchronism with those of the POCT equipment, transmitted through the POCT data channel and then processed in combination with the data gathered by the POCT equipment. Possibly, the fluid sensory device can be used to provide drug/toxicology identification, virus/bacteria discrimination, mold detection.

A commercial POCT which could work as intermediary device, either as originally developed or as customized, could be for example the Toshiba™ Breath Analyser (see http://www.toshiba.co.jp/about/press/2014 03/pr1801.htm).

Fluid sensory device 407 is connected to processing capability 405. It is advantageous that the fluid sensory device be located close to the processing capability, so that ambient temperature/pressure and localization data can be valid for both devices. Likewise for fluid sensory device 410, in relation to processing capability 406. Measurements of the fluid characteristics (identification, concentration) will be performed by the fluid sensory device. The processing capabilities are used to collect this data, possibly preprocess them, collect additional data which are necessary to feed a data modeling tool (see below) transmit this data to the database servers 401, 403, and possibly either directly produce identification data on-site, or receive the identification data from the database servers. It is also possible that the processing capability has a number of models stored in its memory, which are regularly updated. In a number of embodiments of the invention, fluid sensory devices 409, 412 are configured to be capable of collecting identification data (for instance a simple selection in a list of possible analytes) in addition to the sensors' measurements, and transmit this data directly to the database servers in combination with the measurements from their sensors. In these embodiments, the processing capabilities are included in the fluid sensory device. Likewise, a display (or a simple LED) on the fluid sensory device can be available to communicate the results of the identification of the analytes to the user.

According to some variants of the invention, the fluid sensory device can be configured to operate in one of the different modes explained above: through an intermediary processing capability, generic like a smart phone or a PC or specialized like a POCT equipment; or directly in communication with a database server; or purely in a standalone mode, the models being loaded in the memory at the time of purchase of the device by a user.

Figure 5:
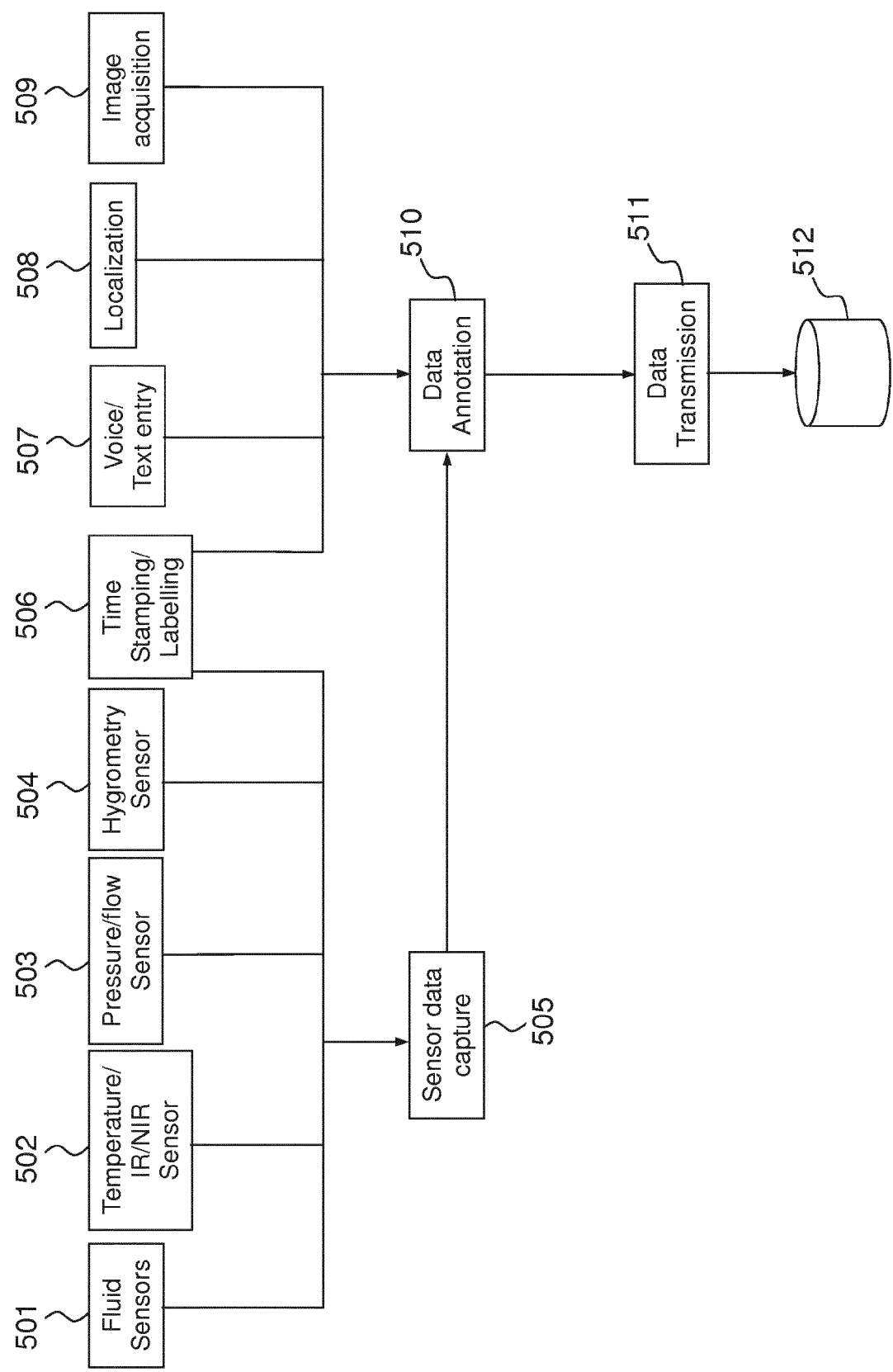
FIG. 5 represents a flow chart of an annotation sub-process for a fluid detection system, in a number of embodiments of the invention.

FIG. 5 represents a flow chart of an annotation sub-process for a fluid detection system, in a number of embodiments of the invention.

In the figure, a number of types of data are represented, but only some of them can be present. The structure of the network, the structure of the data, the procedures to register users, collect data and use data have to be defined by an operator.

At a minimum, fluid (gas/liquid) sensor data 501 are captured by the device. Optionally, but advantageously, temperature sensor data 502, pressure/flow data 503, hygrometry sensor data 504 are also captured and conditioned in a sensor dataset to be sent to the processing capability 405, 406. As a reminder, this processing capability may be embedded in the fluid sensory device or located in its vicinity, in a smart phone, a PC or another type of device, such as a POCT equipment. Optionally, the temperature, pressure, hygrometry data may come from other sensors not located in the fluid sensory device but also connected to the intermediate processing capability. A label 506 consisting of a timestamp or a serial number or a combination of both should be added to the sensor dataset, or first dataset, to allow its precise identification in the database and its combination with the annotation data, when the device is in a modeling operating mode where data is acquired to be input in a database for a modeling purpose.

Thus, using the same label, a second dataset will be created, or appended to the first dataset, said second dataset comprising additional data which will be used to identify the sample which has been the subject of the sensor measurements and to train the model. At a minimum, this annotation 507 should include an identification of the nature of the analyte (tea, coffee, wine, water, etc. . . . ), or of a property (good/bad/neutral; red/white; clean/polluted; etc. . . . ). This annotation can be entered either by selecting an option in a list in an application on the fluid sensory device or the intermediate processing capability. It can also be entered as a free text, or as spoken words. The annotation may be supplemented by localization data 508. The localization data may be provided by the GNSS capability of the smart phone, or entered manually in an application on the PC. Localization data may be useful to calibrate the sensor measurements and/or normalize the ambient temperature/pressure/hygrometry sensor data. GNSS localization data can be replaced by Wifi or cellular network localization when the conditions of reception of the GNSS signals are poor (indoor, multipath environment, etc. . . . ). Also, images 509 can be captured to be appended to the annotation dataset to help identify the analyte or its specific quality, possibly based on color analysis using pattern recognition.

The annotated data 510 are then transmitted 511 to the database server 512.

Figure 6:
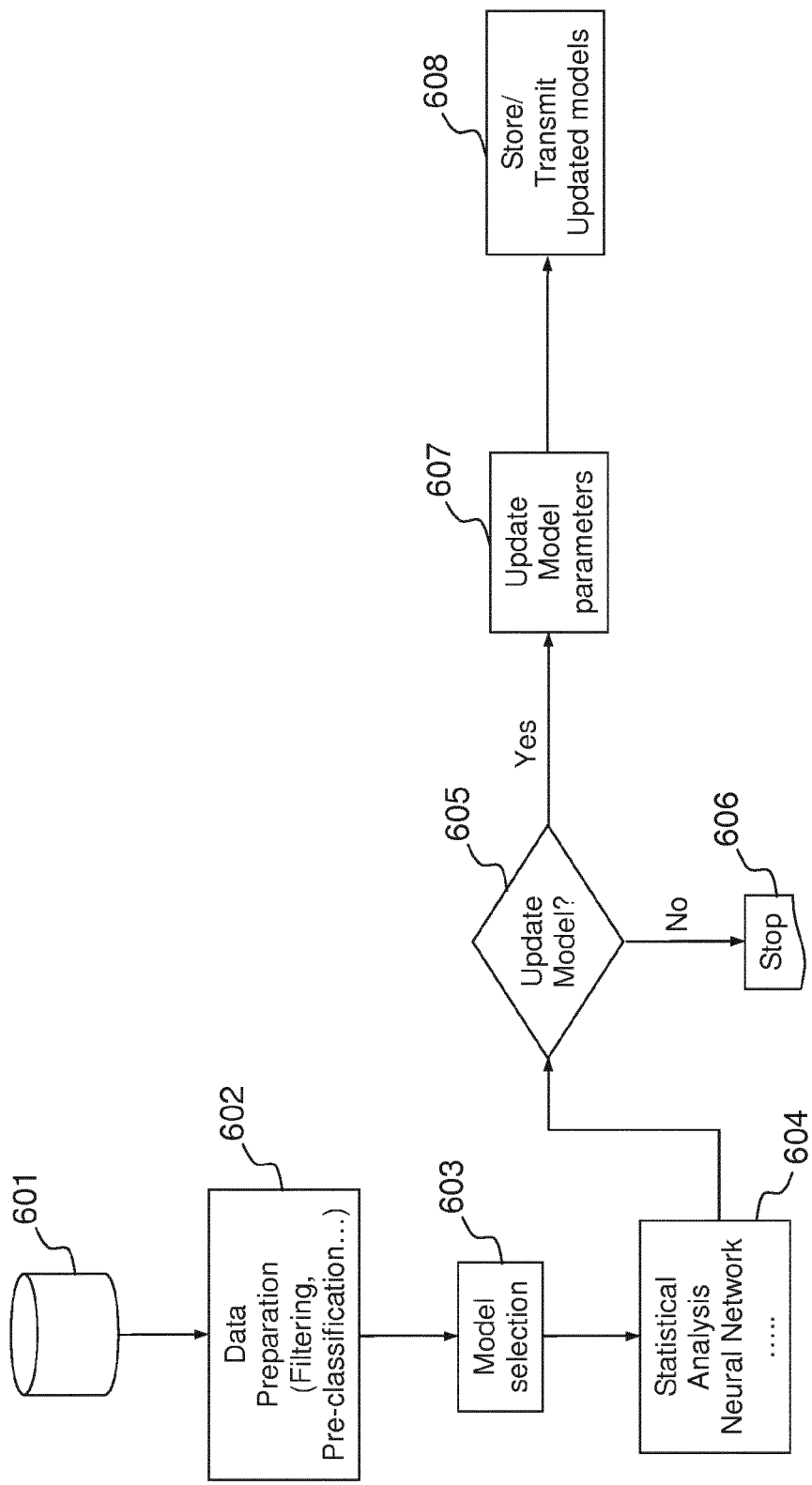
FIG. 6 represents a flow chart of a modeling sub-process for a fluid detection system, in a number of embodiments of the invention.

FIG. 6 represents a flow chart of a modeling sub-process for a fluid detection system, in a number of embodiments of the invention.

At step 601, data stored in the database is retrieved to be processed. At step 602, the data is prepared for being processed. For instance, data may need to be filtered to eliminate datasets from unreliable sources. Data can be pre-classified in different categories depending on the application for which they have been collected. Pre-classification can be fully automated, based on identification of the origin of the data, fully manual, i.e. operator controlled, or semi-automated. At step 603, a type of model is selected based on the type of application (see below). The model may have already been parameterized and the incoming datasets will be added (or not) to the model database. Or the incoming dataset will be used to initialize the parameterization of the model. Then, the incoming datasets are analyzed statistically, the procedure being applied depending on the model selected (step 604). The model building/updating procedure is run (605), with data being rejected (606) or added to the model (607). The updated model is then stored in the database and transmitted to the population of registered users of the applications using this model.

According to the invention, diversity/selectivity of measurements is created by supplying a vast amount of measurement data in known conditions of measurement. The fluid sensory device of the invention is able to work out in variable conditions (temperature, pressure, hygrometry, etc. . . . ). Also, measurements from a device according to the invention can be merged in a database with measurements from other origins, provided that the quality of their conditions of measurements can be certified. For a specific application, the quality of the identification of a definite analyte will depend on whether the model is representative of the condition of measurement of the analyte to be identified. This condition will be better fulfilled if the control variables of the measurements have been cleaned to be free from measurement artefacts. It is therefore advantageous data to use the largest possible amount of measurements, possibly from a large number of sources, to build and improve a model. Here the measurements and sources are necessarily noisy, but the amount of measurements will reduce the information noise.

In this approach, sensor measurements can help customize a model for a user/application. For example, the customization of the model could compensate a measurement bias due to factors such as the location of the measurement (house, office, night club . . . ), the weather or the sensibility of the user to certain odors. The large set of data will allow the classification of a new measurement based on the probability of its identified fingerprint.

A model is built from a large set of sensor measurements combined with all relevant information linked to the measurements through the annotation process (GNSS localization together with the measured or acquired weather, humidity, temperature, latitude, longitude, altitude or other data; user information: gender, age, etc. . . . ). As indicated, some of these parameters can be automatically captured from the intermediary device like GNSS position, weather, etc. . . . . Some other parameters will be kindly requested from the user upon his authorization in order to help tune and adjust the model. In some applications like air quality control, one can think that the measurement can be automatically performed by the device periodically (every hour, every day, etc. . . . ) without any action of the user. An initial set of data will allow the creation of an initial model. This initial model can be further tuned to a specific user by extracting only relevant parameters linked to the applications and/or the user. The tuned model can be further updated with new data from the user measurements or from other data coming from other sources.

The sensor measurements themselves can be normalized, adjusted or calibrated before or after the measure itself. This operation can take place either at the fluid sensory device level prior to the data transfer or in the database server. The sensor can be calibrated via a mathematical calibration model which can be the basis of routine data evaluation. Factory reference and calibration can be done regularly and sent to the cloud for correction of the device data entry. Reference/baseline sample (air for example) can be measured nearby the sample in order to remove/subtract the ambient air matrix from the sample measure. Corrected sample analysis data will then be further sent to the cloud.

Each fluid sensory device on the field might self-calibrate by performing regularly a range of measurement of available samples, allowing recalibration of the device but also normalization of the data.

The size of the sensor information sent to the database servers for evaluation is low relative to the size of the database, so that the transmission and analysis of the information are speedy enough. If practical, the sensor measurements will be performed off-line, stored in the intermediary device and then sent to the database server once the network will allow it.

Once the sample is stored in the database, the information to be analyzed will depend on the application and the model used, as explained below. For instance, one can think of using maximum intensity, intensity at one/several given time(s), slope of the variation of the measurements, key features/remarkable points, point of equilibrium, etc. . . . . Discriminant Function Analysis (DFA) or another statistical model known to a person of ordinary skill may be used to select the variables of importance in a specific application.

Modeling tools to be used for implementing the invention belong to the field of pattern recognition systems. The initial model might be built on available results from either the fluid sensory device of the invention or a lab instrument like an electronic nose or e-nose. It might have a weak recognition index for new unknown samples. However, the addition of a large number of datasets will allow implementing and tuning the model. In this approach, measurements can help customize a model for a user/application.

Different algorithms can be used, alone or in combination, to identify patterns in a large database in a very short time.

A number of statistical models can be used alone or in combination to implement the invention. The inventors have used a number of them, and the selection of the model(s) most likely to yield the best result will be application dependent. Among the models used in the art of pattern recognition, we can cite: Random forests (RF) models, where classes are built from decision trees; Similarity/dissimilarity measurement models, where classes are built from a measure of the dependency (independency) between the sets of measurements.

The inventors have found that a reduced set of models were the most efficient for recognizing patterns which are usual in fluid sensing applications. This reduced set of models comprises:

Fuzzy models: for reference, see for instance, "Fuzzy Models for pattern Recognition", Method that search for structures in Data ISBN 0-7803-0422-5

Artificial neural networks (ANN) models: for reference, see for instance:

"Neural Networks" Theoretical Foundations and Analysis ISBN 0-87942-280-7; "Artificial Neural Networks" Paradigms, applications, and hardware implementations ISBN 0-87942-289-0; "Artificial Neural Network Learning: A Comparative Review" in Methods and Applications of Artificial Intelligence Lecture Notes in Computer Science, Volume 2308, 2002, pp 300-313 'Neural networks and statistical techniques: A review of applications' in Expert Systems with Applications Volume 36, Issue 1, January 2009, Pages 2-17

Support Vector Machine (SVM): for reference, see for instance, "Review and performance comparison of SVM- and ELM-based classifiers" in Expert Systems with Applications Volume 36, Issue 1, January 2009, Pages 2-17

Hierarchical Clustering Analysis (HCA): for reference, see for instance: http://math.stanford.edu/~muellner Adaptive Resonance Theory (ART) is one of the most efficient models for the type of applications of the invention. Adaptive Resonance Theory is a cognitive and neural theory of how the brain autonomously learns to categorize, recognize, and predict objects and events in a changing world. Central to ART's predictive power is its ability to carry out fast, incremental, and stable unsupervised and supervised learning in response to a changing world. ART specifies mechanistic links between processes of consciousness, learning, expectation, attention, resonance, and synchrony during both unsupervised and supervised learning.

For reference, see for instance: "Adaptive Resonance Theory: How a brain learns to consciously attend, learn, and recognize a changing world", Stephen Grossberg, Centre for Adaptive Systems, Boston University, Neural Networks, Elsevier Ltd, 2002; An Embedded system for real time gas monitoring using an ART2 neural network, Jung-Hwan Cho*, Chang-Hyun Shim**, In-Soo Lee+, Duk-Dong Lee*, and Gi-Joon Jeon, School of Electrical Engineering and Computer Science, Kyungpook National University, Daegu, Korea, ICCAS2003 October 22-25

Therefore, to obtain good results for a definite application, it will be important to choose both the most suitable model and the most suitable variables and parameters in the model. By way of example only, to identify odors from a selection of products, the choice of an ART model with the following variables has proven to be efficient:

the maximum change rate of the sensor's response;
the corresponding time in the transit response;
steady state responses at different operation temperatures.

The models can also be applied directly to the measurements and not to variables constructed from the measurements.

More than one statistical model can be applied concurrently on the same measurements or variables constructed from the measurements. Then, a voting or a fusion scheme can be applied, based on a heuristic which may take into account human expertise, and/or the history of the identifications, and/or a mathematical definition of a best fit criteria.

Figure 7:
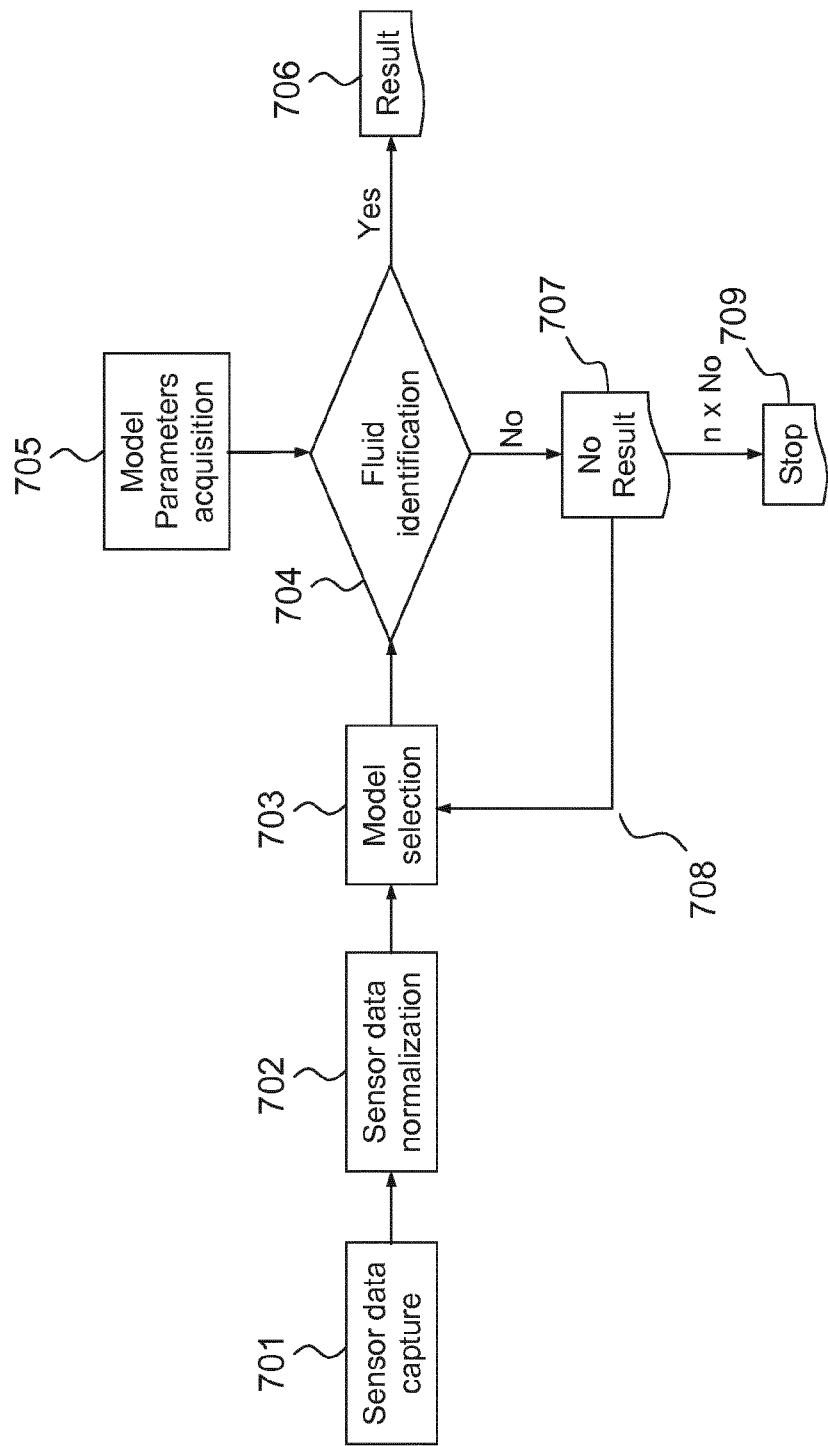
FIG. 7 represents a flow chart of a detection sub-process for a fluid detection system, in a number of embodiments of the invention.

FIG. 7 represents a flow chart of a detection sub-process for a fluid detection system, in a number of embodiments of the invention.

Sensor data is captured at a step 701 using the fluid sensory device of the invention. Depending on the configuration of the device, the data will be processed in the device, sent to an intermediary processing capability or sent to a database server. Sensor data may have to be normalized at a step 702. Then, depending on the application, a model which is fit for processing the dataset will be selected at a step 703. The models database may be resident in the fluid sensory device, the intermediary processing capability or the database server, or split between the three locations. The fluid identification procedure (or the measurement of its concentration) is then carried out at step 704, taking into account the parameters which are associated with the model, at step 705. If the fluid (or its concentration) is identified within a confidence interval, which is set based on the application, the process stops (706) and the result is transmitted to the user (possibly with an indication of the confidence interval). If the identification procedure does not return a result which is within the set confidence level (707), another model may be tried (step 708), with the process being run a number of times which may be set based on the application. When the stop criteria is met without any result within the confidence level, the identification procedure is stopped and the user is informed.

In accordance with certain variants of the preceding embodiment, if the identification procedure does not return a result which is within the set confidence level at step 707, the method may loop back to step 703, at which a new model for the processing of the data set may be selected.

In accordance with certain embodiments, if the identification procedure does not return a result which is within the set confidence level at step 707, the method may loop back to step 702, at which the data may be re-normalized according to an alternative normalization structure.

In accordance with certain embodiments, if the identification procedure does not return a result which is within the set confidence level at step 707, the method may loop back to step 701, at which new data are captured.

It will be appreciated that the three preceding variants are mutually compatible, so that embodiments are envisaged in which the method incorporates two or more of these variants, and furthermore may incorporate different combinations of these variations. For example, a hierarchy may be implemented whereby the method attempts to identify a particular dataset according to a particular number of identification models, then adjusts normalization before retrying the same set of identification models, which may be repeated for a number of different normalizations, before finally capturing new data and recommencing the process.

A number of use cases are presented below.

EXAMPLE 1

Discrimination of Odors

In a use case, four distinct products (lavender, citronella, orange and vanilla are identified with certainty. A sample of the product is place in an arrangement of the type displayed in FIG. 3*b*. The sample should be prepared some time before the measurement. Once the sample is properly conditioned, measurements are performed, the data being sent to a smart phone 405. A plurality of models can then be trained with the data (measurements and/or variables), either on the smart phone, or on a remote server. The annotation data in this use case are quite simple (for example, the user touches the image of the correct product on the screen of the smart phone). Then, once a measurement for each of the four different products have been fed to the model, it is possible to use it to identify one of the four analytes and to display the correct result on the smart phone.

EXAMPLE 2

Determination of a Coffee Origin 2 g of coffee powder are placed in a plate. The fluid sensory device (with static headspace with the cloche-diffusion mode of FIG. 2*a*) is placed in contact with coffee. Measurement is performed by the sensor. Sensor responses are taken either at the steady state, or at remarkable points or after a given time. The steady state will depend in particular on the sensor material. Remarkable points are for instance inflexion points of the sensor resistivity curve as a function of time.

Typically, for type of products of Examples 1 and 2, the steady state is of a few milliseconds or seconds (between 10 and 100 for the type of MOS sensors used). The given time is selected so as to have thermal stabilization of the sensor membrane, this value is linked to the thermal time constant of the membrane materials. All the responses can be taken simultaneously. The obtained value is compared to a database in order to identify the origin of the coffee sample. The database can be located either within the device, in an intermediary processing capability like a smart phone, a tablet or a PC, or in a database server. Results are provided either in the stick or at the intermediary device.

EXAMPLE 3

Breath Smell Analysis

The user is breathing into the device to check the quality of his breath; bad breath corresponds to an unpleasant odor present in the exhaled breath. Bad smell can be due to dental trouble, bacteria present on the back of the tongue, disorders in either ENT (Ear, Nose, Throat), stomach . . . . But also the origin can be tracked to lack of activity, life quality, food intake . . . . This bad smell can cause the user social anxiety or depression.

Sensor responses are taken either at the steady state, or at remarkable points or after a given time. All of them can be taken simultaneously providing a pertinent combination of variables which is sent to the cloud for further identification and model adjustment. The initial model is built with control groups of known unhealthy persons and healthy persons with a good breath odor. The model is further implemented with all received data from the different users to define a better estimation of the results. The model implementation will be further tuned depending on the person origin, food intake, life quality. The large data set of the model will allow an identification of the origin of the bad smell, informing the user on different possible causes and recommendations for a better breath odor quality.

Body fluids (blood, plasma, urine, etc. . . . ) or body odors can also be analyzed.

The examples disclosed in this specification are only illustrative of some embodiments of the invention. They do not in any manner limit the scope of said invention which is defined by the appended claims.

The invention claimed is:

1. A portable fluid sensory device for characterizing an analyte having a gas phase and a liquid phase based on a model, said fluid sensory device comprising:
    a gas sensor for sensing said gas phase of said analyte and a liquid sensor for sensing said liquid phase of said analyte at the same time, said gas sensor and said liquid sensor generating a fluid sensing signal;
    a first controller configured to identify said analyte by processing said fluid sensing signal on the basis of said model and to output a result;
wherein said first controller is further configured to generate a first dataset representative of the fluid sensing signal, and said first dataset further comprises a label comprising a timestamp or a serial number characterizing the fluid sensing signal,
and wherein said first controller is further configured to combine said first dataset by reference to said label with a second dataset comprising context data collected at the same time as the first data set, said context data characterizing the fluid sensing signal and comprising at least one of a text, a sound and an image, said first controller being further configured to use the second dataset to train the model;
    a communication interface configured to send to a remote processing device said second dataset representative of the fluid sensing signal; and to obtain said model from a remote processing capability; and
wherein said fluid sensory device having an elongated form factor, with a distal end comprising a contact surface of the liquid sensor and a proximal end comprising an entry port of said gas sensor, wherein the fluid sensory device is adapted to be inserted substantially vertically into a cup containing said analyte in a first orientation to perform said sensing of said gas phase of said analyte by said gas sensor via said entry port, and reversed to be inserted substantially vertically into said cup containing said analyte in a second orientation to perform said sensing of said liquid phase by said contact surface of the liquid sensor.

2. The fluid sensory device of claim 1, wherein the gas sensor comprises a single semiconducting metal-oxide element.

3. The fluid sensory device of claim 1, wherein the gas sensor comprises one of an array and a stack of a plurality of semiconducting metal-oxide elements.

4. The fluid sensory device of claim 3, further comprising a source of ultraviolet light for illuminating at least some of the plurality of semiconducting metal-oxide elements.

5. The fluid sensory device of claim 1, wherein the gas sensor comprises a micro gas chromatograph.

6. The fluid sensory device of claim 1, having an entry port with a bell shaped extension.

7. The fluid sensory device of claim 1, wherein the liquid sensor comprises a micro HPLC column.

8. The fluid sensory device of claim 1, wherein an entry port is covered with a removable cap which is usable as said cup for receiving a sample to be analyzed and the fluid sensory device.

9. The fluid sensory device of claim 1, further comprising an additional sensor selected in a group comprising temperature sensors, flow sensors and hygrometry sensors, an output of the additional sensor being transmitted to the processing capability.

* * * * *